United States Patent [19]

Saupe et al.

[11] 4,151,647
[45] May 1, 1979

[54] DENTAL UNITS

[75] Inventors: Martin Saupe, Mittelbiberach; Stefan Beier, Biberach, both of Fed. Rep. of Germany

[73] Assignee: Kaltenbach & Voigt, Biberach, Fed. Rep. of Germany

[21] Appl. No.: 762,783

[22] Filed: Jan. 25, 1977

[30] Foreign Application Priority Data

Feb. 4, 1976 [DE] Fed. Rep. of Germany ....... 2604246

[51] Int. Cl.² ............................................ A61C 19/02
[52] U.S. Cl. ..................................................... 32/22
[58] Field of Search ............... 32/22, DIG. 3; 251/33, 251/30, 138

[56] References Cited

U.S. PATENT DOCUMENTS

| 2,834,609 | 5/1958 | Bertrand | 251/30 |
| 2,919,708 | 1/1960 | Horne | 251/30 |
| 3,090,592 | 5/1963 | Fleer | 251/30 |
| 3,488,849 | 1/1970 | Lieb et al. | 32/22 |
| 3,620,658 | 11/1971 | Tappin | 251/30 |
| 3,791,619 | 2/1974 | Pett | 251/30 |
| 3,801,063 | 4/1974 | Holmes et al. | 251/30 |
| 3,994,069 | 11/1976 | Hohmann | 32/22 |

FOREIGN PATENT DOCUMENTS

| 1297808 | 6/1969 | Fed. Rep. of Germany | 32/22 |
| 2037181 | 2/1972 | Fed. Rep. of Germany | 32/22 |
| 2339824 | 2/1975 | Fed. Rep. of Germany | 32/22 |

Primary Examiner—Russell R. Kinsey
Assistant Examiner—John J. Wilson
Attorney, Agent, or Firm—Haseltine, Lake & Waters

[57] ABSTRACT

A dental unit having pressure-medium operated handpieces, a holder for each handpiece, a control unit operable to control the supply of pressure medium to each handpiece, and switch means associated with each holder and with said control unit, each switch means being operable upon removal of the respective handpiece from its holder to initiate operation of the control unit for the supply of pressure medium to the handpiece.

The control unit comprises a control block corresponding to each handpiece, a first passage extending through the control blocks to supply pressure medium for operating the handpieces, a second passage in each control block communicating with a respective handpiece, a diaphragm controlling the communication between the first passage and each second passage, a control chamber controlling the operation of the diaphragm, the control chamber being charged with control pressure medium in order to move the diaphragm to a position blocking communication between the first passage and the respective second passage, a venting arrangement for venting each control chamber, and an electrically operated closure element cooperating with each venting arrangement, the closure element being controlled by the respective switch means in order to vent the control chamber when one of the handpieces is removed from its holder so that the handpiece is ready to be supplied with pressure medium via the first passage and the second passage.

6 Claims, 4 Drawing Figures

DENTAL UNITS

DESCRIPTION OF THE PRIOR ART

It is known from German specification No. 2,231,735 to provide a dental unit having a plurality of handpieces each mounted removably in a holder and provided with energy supply hoses or pipes leading into the unit. One or more of the handpieces is adapted to be driven by pressure air and one or more by electrical current, and the handpieces are adapted to be cut-in and out by a common starter, there being associated with each handpiece a switch operable upon extraction of the handpiece from its holder and which cuts-in in preparatory manner a supply of energy for the handpiece i.e. pressure air and/or electrical current. Thus, upon appropriate actuation of the common starter, the extracted handpiece i.e. the working handpiece, starts-up whereas the further handpieces which are disposed in their holders or extracted i.e. the inoperative handpieces, remain at a standstill.

The handpieces may be designed to be straight or angled, and conventionally the switches are arranged in or at the holders which are of for example "quiver" or sheath form.

In the known unit, the switches are designed as transmitters controlling logic-switched components connected sequentially of them, the component group of each transmitter being switched with (or linked to) the further component groups, for shutting down the inoperative handpieces when the working handpiece is extracted. With this arrangement, starting-up of the handpieces operated with different energies i.e. pressure air and also pressure water and electrical current, is prepared or programmed with the aid of electrical control means constituting the energy supply element, and this is extremely costly with reference to pressure air operated handpieces.

A similar dental unit is also known from German Auslegeschrift No. 2,038,976.

Finally, it is known from German Offenlegungsschrift No. 2,339,824, for individual control of handpieces operated by pressure air or electrical current, to provide a control block in each particular instance, and to assemble the said control blocks or units (corresponding in number to the number of handpieces) in close arrangement to constitute a control unit provided with a passage duct extending through all the control blocks and conveying the supply media for the handpieces, from which said passage duct there branches-off in each control block a branch duct into the flow path in which there is inserted a diaphragm or membrane associated with which is a control chamber provided on its side located opposite the incident-flow supply medium, which said control chamber is adapted to be subjected to the action, via a control line, of control pressure air for effecting blocking of the throughflow of the supply medium through the branch duct, there being provided in the control line a venting aperture which, in its open position, effects release of the supply medium through-flow through the branch duct. In the case of this known design, the said venting aperture is formed by the end of a venting line connected to the control line and extending as far as the holder of the particular handpiece. There, there is provided, a switch actuable by the handpiece on extraction out of or introduction into the holder, a closure valve adapted to be closed or sealed by the handpiece disposed in its inoperative position in the holder and, on the handpiece being removed, adapted to be opened by the air pressure building-up from a pressure air source. Thus, when the closure valve is opened, no control air flows to the control chamber.

In the case of this known design, the pneumatic control unit assembled from the individual control blocks has proved very satisfactory. However, the venting line connected to the control line of each individual control chamber and extending as far as the holder of the particular handpiece represents, with the closure valve associated with the end of each venting line, a relatively high structural outlay which nevertheless could be justified in the case of a dental unit having handpieces operated exclusively by pressure air.

It is an object of the invention to provide a dental unit of the type mentioned at the outset, i.e. having handpieces operated by pressure air and operated by electrical current, wherein the preparatory cutting-in or programming at least of starting-up of the pressure air driven handpieces, and also, in preferred development, the preparatory cutting-in or the feed of coolant or other supply pressure media both to the handpieces driven with pressure air and also to those driven with electrical current, is made possible using the known and well-tried pneumatic control unit, but avoiding a costly closure or sealing device for the venting aperture of the control lines.

SUMMARY OF THE INVENTION

According to the invention there is provided a dental unit comprising:

dental handpieces operable by pressure medium;

a holder for each handpiece;

a control unit operable to control the supply of pressure medium to each handpiece;

and switch means associated with each holder and with said control unit, each switch means being operable upon removal of the respective handpiece from its holder to initiate operation of the control unit for the supply of pressure medium to the handpiece;

in which the control unit comprises:

a control block corresponding to each handpiece;

a first passage extending through said control blocks and communicable with a supply of pressure medium for operating the handpieces;

a second passage in each control block communicable with said first passage for supplying pressure medium to the handpiece corresponding to the control block;

a diaphragm associated with each of said second passages and operable to control the communication between the respective second passage and said first passage;

a control chamber provided on one side of each diaphragm;

a control line communicable with each control chamber for supplying a control pressure medium to the control chamber thereby to operate the diaphragm to effect blocking of communication between said first passage and said second passage;

venting means communicating with each control line for discharging control pressure medium from the respective control chamber thereby to operate the diaphragm to permit communication between said first passage and said second passage when the venting means is open;

and an electrically operable closure device cooperable with each of said venting means, said closure device being controlled by one of said switch means in order to effect opening of the venting means when a respective handpiece is removed from its holder.

The operation of the closure device by the switch means, following removal of a particular handpiece from its holder, can, therefore, be employed for calling in a pre-programmed condition of the working handpiece, and also can effect blocking relative to the other inoperative handpieces.

By providing electrically operated closure devices, it is merely necessary to extend in each particular instance a simple exciter circuit comprising thin wires from the closure element to the switch means, instead of a voluminous control air venting line which is rigid and therefore liable to breakdown due to risk of crushing. Control of the closure element with the aid of an electrical current supplying the exciter circuit does not normally represent a supplementary outlay, because in the preferred embodiment the dental unit includes handpieces operated with pressure and also handpieces operated with electrical current, so that in any case it is connected to a source of electrical current.

The preparatory cutting-in or programming of starting-up of the handpieces operated with electrical current can be effected in known, simple manner, with the aid of electrical current supply elements or electrical control elements, but at the same time employing the above-mentioned exciter circuit.

A preferred design which is especially simple and space-saving comprises providing a venting aperture which is constituted by the open end of a venting line extending-out from a control line leading to the control chamber and projecting at its open end out of a free side wall of the control block, the closure element being arranged adjacent said open end.

One embodiment of the closure element may be provided by an electromagnetically actuable closure element constituted by a core made from magnetisable material and mounted to be displaceable in a stationary coil provided with an exciter winding, which said core is displaced, on excitation taking place, against the effect of a restoring spring, into a position releasing the venting aperture and, in the case of non-excitation, under the influence of the restoring spring into sealing abutment at the venting aperture.

A further embodiment is provided by an electromagnetically actuable closure element having a core made from magnetisable material and provided with an exciter coil, which said core extends parallel to and with spacing adjacent a lateral wall of the (square-form) control block, and is retained with one of its ends by a stationary strap made from magnetisable material, whereas the other end of the core is disposed, in the case of non-excitation, in spaced relationship relative to the free end of a one-armed lever made from magnetisable material and extending substantially transversely of the core, which said lever is so articulated to a stationary joint or hinge that the lever, on the core being excited, due to the magnetic attraction force of the latter, oscillates against the action of a restoring spring into sealing abutment at the venting aperture and, in the case of non-excitation of the core, under the influence of the restoring spring, swings back into the position releasing the venting aperture, the strap and the lever or the joint or articulation means thereof being connected by a component made from magnetisable material. With this arrangement, the component made from magnetisable material may be constituted by the control block itself, and in this case the strap and the lever joint may be arranged at the control block.

Furthermore, the electromagnetically actuable closure element may have a core made from magnetisable material and provided with an exciter winding, which said core extends parallel to and in spaced relationship adjacent to the lateral wall formed with the venting aperture of the square-form control block, and is secured with both its ends to two stationary straps made from magnetisable material and extending transversely of the core, which said straps end before the lateral wall of the control block, one of the two straps being provided at this end with a one-armed lever made from magnetisable material and pivotal about a joint, which said lever in the event of non-excitation of the core swings under the influence of a restoring spring into sealing abutment at the venting aperture and, on excitation of the core, swings-back against the action of the restoring spring into a position releasing the venting aperture.

Expediently, the electromagnetically actuable closure element is provided with a packing passing into abutment at the venting aperture.

The control unit can, apart from the passage duct conveying the driving pressure air for the handpieces driven by pressure air, also be provided with further passage ducts extending through all the control blocks, and conveying pressurised supply media such as cooling air, cooling water or the like, both for the handpieces driven by pressure air and also for those driven by electrical current, from which said further passage ducts there branches-off in the particular control block associated with each handpiece a branch duct connected with the energy supply hose of the particular handpiece and into the flow path of which there is inserted a diaphragm associated with which is a control chamber provided on its side opposite the incident-flow supply medium and connected with the control line of the remaining control chambers.

DESCRIPTION OF PREFERRED EMBODIMENT

Figure 1:
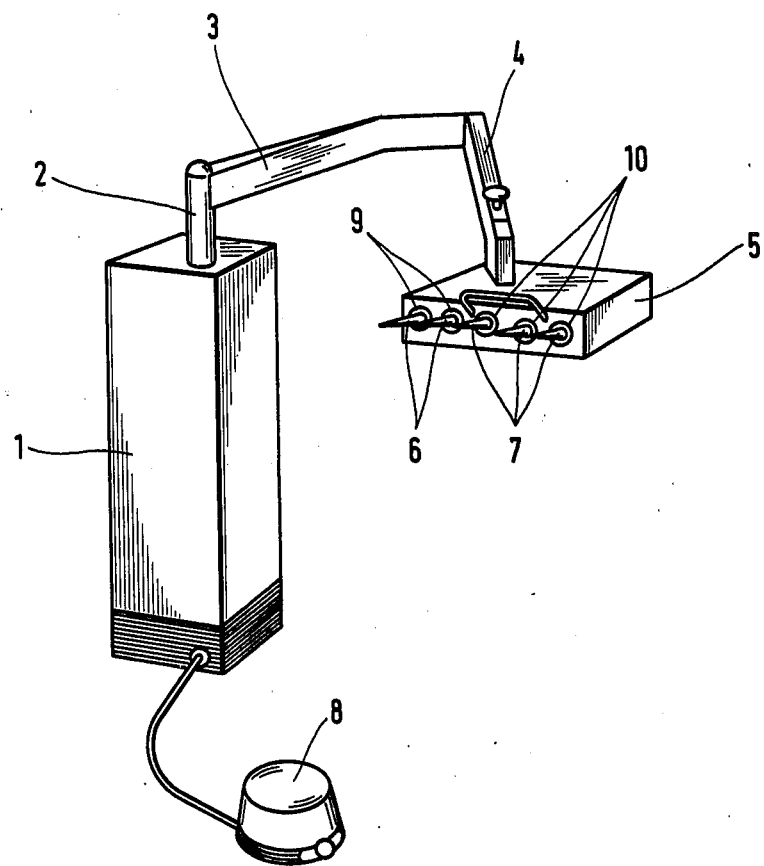
FIG. 1 is a diagrammatic illustration of a dental unit in accordance with the invention.

Referring to FIG. 1, reference numeral 1 designates the apparatus stand or column of a dental device designed as a unit, at the other side of which, with the aid of a vertical shaft 2, a pivot arm 3 is mounted for pivotal movement in a horizontal plane. The pivot arm 3 has an arm extension 4 articulated to the pivot arm 3 so as to be pivotal in both a horizontal and also a vertical plane. Arranged in per se known manner at the forward end of the arm extension 4 is a receiving box 5 for substantially horizontally extractable dental handpieces 6, 7. The receiving box 5 is articulated to the free end of the arm extension 4 in such manner that it is always located in the horizontal position shown, independently of the relative pivoting positions of the arm 3 and extension 4.

FIG. 1 shows a starter 8, designed as a pedal starter and with the aid of which the handpieces 6, 7 can be cut-in and out. The handpieces 6, 7 are (as indicated for a typical handpiece 6 shown in FIG. 2) provided with energy supply hoses 11 debouching into holders 9, 10 of the receiving box 5 of the unit, and are mounted to be movable in and also extractable from the holders 9, 10. In the illustrated example, the handpieces 6 are adapted to be driven by pressure air and the handpieces 7 by electrical current. The handpieces 6 may be air turbine handpieces and/or air motor handpieces and the handpieces 7 may be handpieces having a built-in, miniature electrical motor.

Figure 2:
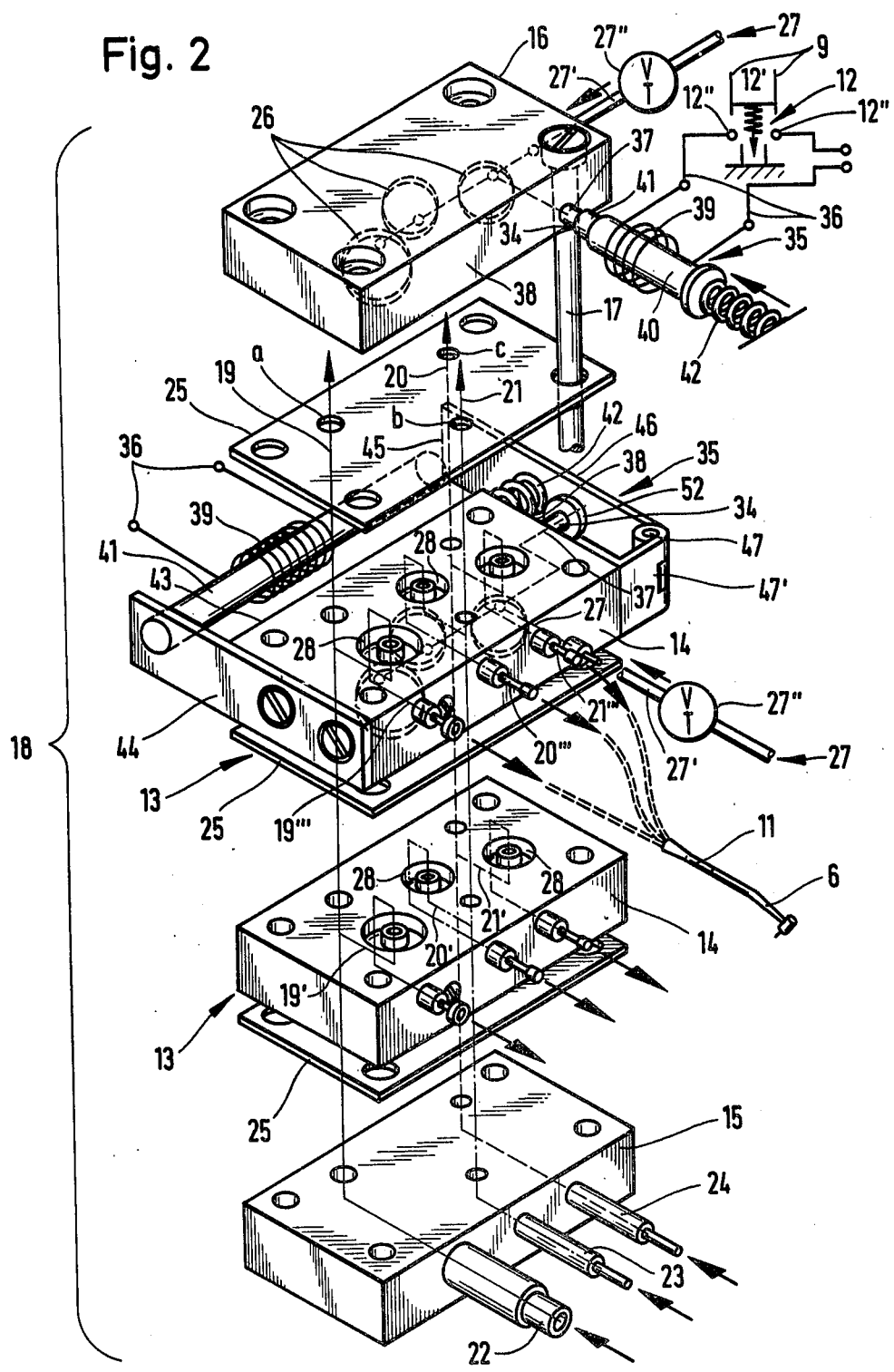
FIG. 2 is an exploded view of a control unit of the dental unit.

The holders of the handpieces 6 (driven by compressed air) are designated 9 and the holders of the handpieces 7 (driven by electrical current) are designated 10. Turning to FIG. 2, one of the holders 9 is shown diagrammatically.

Associated with each handpiece 6, 7 is a switch 12 adapted to be tripped following removal of the handpiece from the holder 9, 10.

Referring to FIG. 2, there is shown only diagrammatically for a handpiece 6 operated by pressure air, a switch 12 which cuts-in in preparatory manner an energy supply element 13 for feeding driving pressure air to the handpiece 6 when extracted from its holder. On appropriate actuation of the starter, the extracted handpiece 6, i.e. the working handpiece, starts-up whereas the further handpieces disposed in their holders or extracted (i.e. the inoperative handpieces) remain at a standstill.

Figure 3:
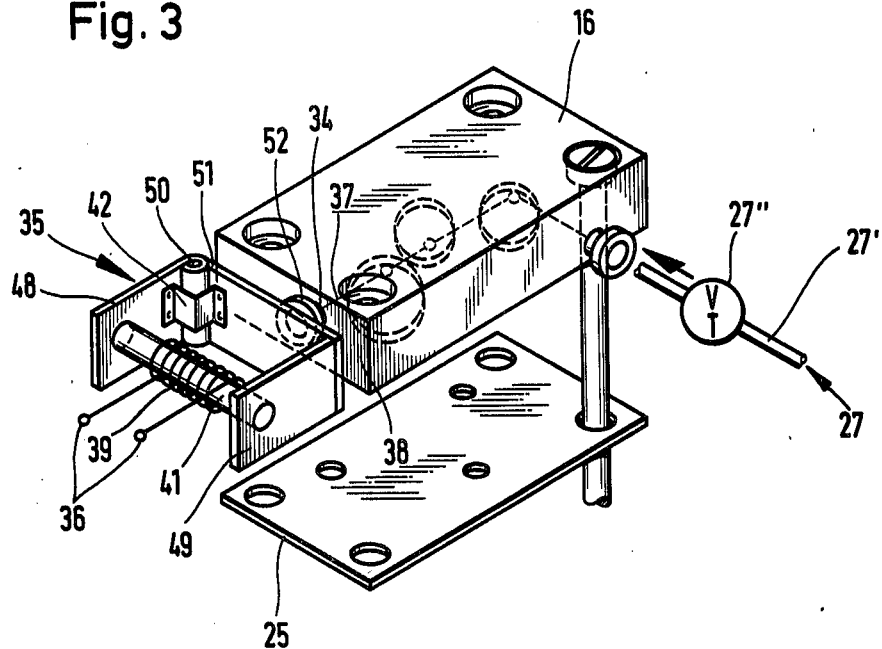
FIG. 3 is an exploded view of an alternative arrangement for a control block of the control unit shown in FIG. 2.

As FIGS. 2 and 3 show, the energy supply elements 13 for the handpieces 6 (operated by pressure air) each comprise a respective control block 14. Upper and lower control blocks 14 are assembled to form a control unit 18 having an input block 15 and an end block 16, by means of screws 17 which extend-through.

The control unit 18 is, referring to FIG. 2, formed with first passages in the form of passage ducts 19, 20, 21 extending from the input block 15 through the two control blocks 14 from below upwardly and carrying supply media for the handpieces 6 (or 7). The supply medium for the passage duct 19 passes through an input (or inlet) port stub 22, the supply medium for the passage duct 20 through an input port stub 23 and the supply medium for the passage duct 21 through the input port stub 24, into the input block 15. In use, the passage duct 19 may convey pressure air for driving the handpieces 6, the passage duct 20 may convey cooling water, and the passage duct 21 may convey cooling air, for example for forming a spray.

Disposed in each particular instance between the two control blocks 14 and also between the lower control block 14 and the end block 15 and the upper control block 14 and the input block 16 is, for sealing purposes, a respective diaphragm 25 formed with apertures a, b, c for the passage ducts 19, 20, 21.

In each of the two control blocks 14, there branches-off in each particular instance from the passage ducts 19, 20, 21 second passages in the form of a branch duct 19', 20', 21', which, according to FIG. 2, is connected with the energy supply hose 11 of the associated handpiece 6, the starter 8 (FIG. 1) being interposed (in a manner not shown) upstream of the handpiece 6.

Figure 4:
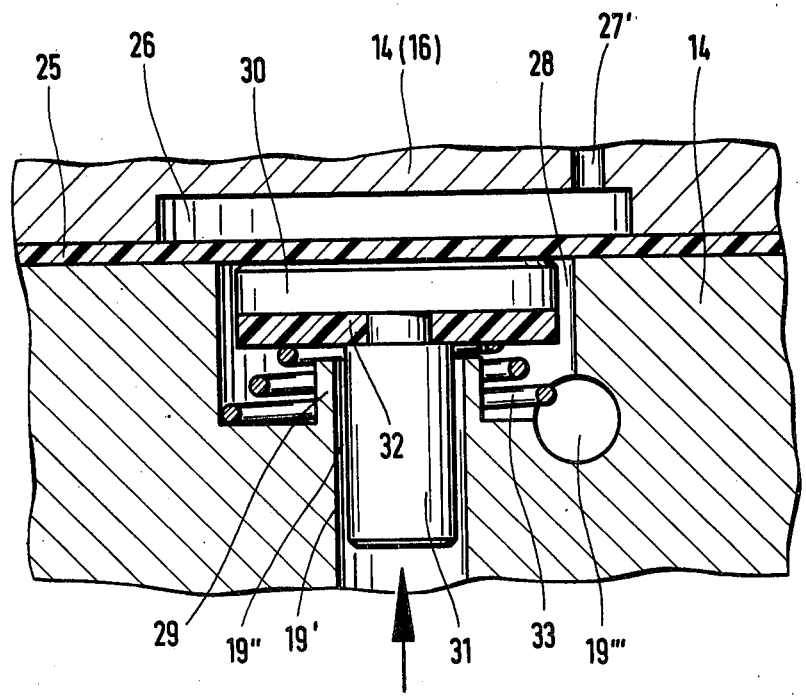
FIG. 4 is an enlarged sectional view of two adjacent control blocks of the control unit.

As will be clear in particular from FIG. 4, which illustrates the path of the branch line 19' through either one of the blocks 14, the diaphragm 25 is connected in the flow path of the branch duct 19'. On the side remote from the branch duct 19', i.e. on the side of the diaphragm 25 located opposite the incident-flow pressure medium, there is a control chamber 26 adapted to be subjected to the action of pressure air (control pressure medium) by means of a pressure air control line 27' connected to a pressure air source 27. Arranged in the control line 27' is also a throttle 27".

A respective diaphragm 25 is simultaneously arranged as a packing or seal between each of the adjacent blocks 15 and 14, 14 and 14, and 14 and 16.

Referring to FIGS. 2 to 4, the control chamber 26 is in each instance provided in the upper one of the blocks 14 or the block 16, whereas there is provided on the side of the diaphragm 25 located opposite the control chamber 26, in both the upper and the lower block 14, a valve chamber 28 which is open towards the diaphragm 25 and which has a seat 29 for a freely displaceable valve body 30 actuable in the closure sense by the diaphragm 25.

The valve chamber 28 in the upper block 14 co-operates with one side of the diaphragm 25 between the upper block 14 and the block 16, whereas the control chamber 26 in block 16 co-operates with the other side of the diaphragm 25. Similarly, the control chamber 26 in the upper block 14 co-operates with one side of the diaphragm 25 between the upper and lower blocks 14, whereas the valve chamber 28 in the lower block 14 co-operates with the other side of the diaphragm.

The valve body or valve member 30 is designed as a valve disc and has a guide shaft 31 extending into the "arriving" element 19" of the branch duct 19'. Provided below the valve body 30 designed as a valve disc is a sealing ring 32. Furthermore, there is associated with the valve body 30 a compression spring 33 acting on it in a direction away from the valve seat 29.

The portion of each branch duct 19', 20', 21' extending away from the valve chamber 28 and connected with the energy supply hose 11 of the particular handpiece is designated 19''', 20''', 21'''.

It is furthermore apparent from FIGS. 2 and 3 that a venting aperture 34 of each control chamber 26 has associated with it an electromagnetically actuable closure element 35 having an exciter circuit 36 which is controlled by the particular switch 12 associated with each handpiece. In FIG. 2, only one handpiece 6 is shown, which is associated with upper block 14. Also, the switch 12 shown in FIG. 2 controls the closure element 35 which is associated with end block 16. The switch 12 is designed as a switch moveable to close or to interrupt the exciter circuit 36. When the handpiece 6 is out of the holder 9, the switching element 12' is loaded so that it passes into abutment at the switching contact 12" and the switch 12, and therewith the exciter circuit 36, is closed. FIG. 2 also shows a closure element 35 associated with a venting aperture 34 of upper block 14, the closure element being controlled by a switch (not shown) which functions in an opposite manner to the switch 12 associated with end block 16. The switch (not shown) is operated by the handpiece 6 (also not shown) associated with lower block 14, but in opposite manner in that the respective circuit 36 is de-energised by opening of the switch when the handpiece is removed from its holder 9.

Each venting aperture 34 is, as FIGS. 2 and 3 show, constituted by the open end of a venting line 37 extending away from a control line 27 communicating with the control chamber 26. Through the agency of its open end, the venting line 37 projects out of a free side wall 38 of the upper control block 14 or of the end block 16, the electromagnetically actuable closure element 35 being arranged in front of this open end.

Referring to FIG. 2, the closure element 35 associated with the end block 16 serves to control the communication between the branch ducts 19', 20', 21' and their outward extensions 19''', 20''', 21''' of the upper control block 14, whereas the closure element 35 associated with the upper control block 14 serves similarly to control communication in the lower control block 14. Two embodiments of closure members 35 for end block 16 are shown in FIGS. 2 and 3, and one embodiment for upper block 14 is shown in FIG. 2.

The electromagnetically actuable closure element 35 associated in FIG. 2 with the end block 16 is constituted directly by a core 41 made from magnetisable material and mounted to be displaceable in a stationary coil 40 provided with an exciter winding 39. On excitation of the winding 39, the core 41 travels against the action of a restoring spring 42 designed as a compression spring into a position releasing the venting aperture 34 and, in the case of non-excitation, it travels under the action of the restoring spring 42 into sealing abutment at the venting aperture 34.

The electromagnetically actuable closure element 35 which, referring to FIG. 2, is associated with the upper control block 14, has a core 41 made from magnetisable material and provided with an exciter winding 39. The core 41 which is designed to be of rod-form extends parallel to and in spaced relationship adjacent a side wall 43 of the square-form control block 14. Through the agency of one of its ends, the core 41 is retained by a strap 44 secured to be stationary at the control block 14 and made from magnetisable material, whereas the other end of the core 41 (on non-excitation of the winding 39) extends in spaced relationship relative to the free end 45 of a one-armed lever 46 made from magnetisable material and extending substantially transversely of the core. The lever 46 is pivoted to a stationary articulation means 47 in such a way that, on excitation of the winding 39 or of the core 41, due to the magnetic attraction force of the latter, against the action of a restoring spring 42 designed as a compression spring, it pivots into sealing abutment against the venting aperture 34. In the event of non-excitation of the core 41, the lever 46 swings, under the influence of the restoring spring 42, back into the position freeing the venting aperture 34, the strap 44 and the lever 46 of the articulation means 47 thereof being connected by a component made from magnetisable material.

The last-mentioned component is, in the case of the example of embodiment described, constituted by the control block 14 itself which, in this case, is made from magnetisable material, and as already stated the strap 44 and the articulation means 47 of the lever 46 or the carrier 47' therefor are secured to the control block 14. The component can (in a manner not shown) be constituted by a yoke connecting the strap 44 with the carrier 47 secured to the control block.

The alternative closure element 35 (shown in FIG. 3) associated with the end block 16 has, again, a core 41 made from magnetisable material and provided with an exciter winding 39. The core 41 extends parallel to and in spaced relationship adjacent the lateral wall 38, formed with the venting aperture 34, of the square-form end block 16. Through the agency of its two ends, the core 41 is secured to two straps 48, 49 made from magnetisable material and extending transversely of the core. The straps 48, 49 terminate in spaced relationship a short distance before the lateral wall 38 of the end block 16. The left-hand strap 48 in FIG. 3 is, at the end disposed in spaced relationship before the lateral wall 38, provided with a one-armed lever 51 made from magnetisable material and pivotal about a hinge or joint 50. The lever 51 pivots, in the event of non-excitation of the core 41, under the influence of a restoring spring 42 designed as a compression spring, into sealing abutment at the venting aperture 34. In the event of excitation of the core 41, the lever 51 pivots, against the action of the restoring spring 42, back into a position wherein it frees the venting aperture 34.

The lever 46 in FIG. 2 and also the lever 51 in FIG. 3 is provided with a packing 52 passing into abutment at the venting aperture 34. Also the end of the core 41 facing the end block 16 (in the upper view according to FIG. 2) can be provided with such a packing.

As will be evident from FIG. 4, which illustrates the arrangement of a control chamber 26 on one side of a diaphragm 25 (with respect to end block 16 and upper block 14, or upper block 14 and lower block 14) the supply of control pressure medium to the chamber 26 will result in downward movement of the piston 30 so that seal 32 engages the seat 29 and thereby interrupts communication between the first passage (19,20,21) and the outlets (19''', 20''', 21''') to the handpieces 6. When one of the handpieces 6 is removed from its holder 9, the respective switch (12) controls the circuit 36 so that the chamber 26 can be vented via the venting aperture 34 which is now opened by the closure element 34. This then enables the piston 30 to move upwardly to establish communication between the "first passage" and the appropriate outlet to the handpiece so that the latter can receive a supply of pressure medium when the starter 8 is operated.

The control unit 18 can, apart from the passage duct 19 conveying the driving pressure air for the handpieces 6 driven by pressure air, and apart from the passage ducts 20, 21 conveying supply media such as cooling air, cooling water, hot water or the like for the said handpieces 6, also be provided with further passage ducts (not shown) for conveying supply media of the type mentioned for the handpieces 7 driven by electrical current, a supplementary control block being provided for each of these handpieces 7. These supplementary control blocks may be combined to a separate control unit. The aforementioned, further passage duct (not shown) then also have in the individual control blocks branch ducts which, with reference to preparatory cut-in of inflow of the supply media conveyed in them to the handpieces 7, are designed in the same manner as in the case of the embodiments according to FIGS. 2 to 4.

We claim:
1. A dental unit comprising:
dental handpieces operable by pressure medium;
a holder for each handpiece;
a control unit operable to control the supply of pressure medium to each handpiece;
and switch means associated with each holder and with said control unit, each switch means being operable upon removal of the respective handpiece from its holder to initiate operation of the control unit for the supply of pressure medium to the handpiece;
said control unit comprising:

a control block corresponding to each handpiece;
a first passage extending through said control blocks and communicable with a supply of pressure medium for operating the handpieces;
a second passage in each control block communicable with said first passage for supplying pressure medium to the handpiece corresponding to the control block;
a diaphragm associated with each of said second passages and operable to control the communication between the respective second passage and said first passage;
a control chamber provided on one side of each diaphragm;
a control line cmmunicable with each control chamber for supplying a control pressure medium to the control chamber to operate the diaphragm for blocking of communication between said first passage and said second passage;
venting means communicating with each control line for discharging control pressure medium from the respective control chamber for operating the diaphragm to permit communication between said first passage and said second passage when the venting means is open;
an electrically operable closure device cooperable with each of said venting means, said closure device being controlled by one of said switch means for opening of the venting means when a respective handpiece is removed from its holder said control line having a diaphragm controlled separately by pressure medium, one closure device influencing pressure conditions in said control chamber across said diaphragm;
said venting means comprising a venting line housed in said control unit and communicating with said control chamber, and a venting aperture at one end of said venting line, said closure element being arranged adjacent said venting aperture;
said electrically operated closure element comprising a magnetizable core and an exciter winding, said core extending parallel and in spaced relation to one wall of the control unit, a strap holding one end of said core, a layer arranged adjacent an opposite end of said core for pivotal movement upon energization of the coil so as to close said venting aperture, and a restoring spring for biasing the lever to an open position with respect to the venting aperture.

2. A dental unit according to claim 1, wherein one of said control blocks, a pivot of said lever, and said strap are made of magnetizable material, said pivot and said strap being mounted on said one control block.

3. A dental unit according to claim 1, wherein each closure element includes a packing for sealing engagement with said venting aperture.

4. A dental unit according to claim 1 and including electrically operable handpieces, the control unit including control blocks associated with said electrically operated handpieces, a plurality of coolant passages extending through all of the control blocks of the control unit for conveying coolant media to said handpieces, branch passages provided in said control blocks and communicable with said coolant passages, a diaphragm arranged in the flow path between each branch passage and one of said coolant passages to control the communication therebetween, a control chamber controlling the operation of the diaphragm, and means connecting said control chamber with a control line of the remaining control chambers.

5. A dental unit comprising:
dental handpieces operable by pressure medium;
a holder for each handpiece;
a control unit operable to control the supply of pressure medium to each handpiece;
and switch means associated with each holder and with said control unit, each switch means being operable upon removal of the respective handpiece from its holder to initiate operation of the control unit for the supply of pressure medium to the handpiece;
said control unit comprising:
a control block corresponding to each handpiece;
a first passage extending through said control blocks and communicable with a supply of pressure medium for operating the handpieces;
a second passage in each control block communicable with said first passage for supplying pressure medium to the handpiece corresponding to the control block;
a diaphragm associated with each of said second passages and operable to control the communication between the respective second passage and said first passage;
a control chamber provided on one side of each diaphragm;
a control line communicable with each control chamber for supplying a control pressure medium to the control chamber to operate the diaphragm for blocking of communication between said first passage and said second passage;
venting means communicating with each control line for discharging control pressure medium from the respective control chamber for operating the diaphragm to permit communication between said first passage and said second passage when the venting means is open;
an electrically operable closure device cooperable with each of said venting means, said closure device being controlled by one of said switch means for opening of the venting means when a respective handpiece is removed from its holder said control line having a diaphragm controlled separately by pressure medium, one closure device influencing pressure conditions in said control chamber across said diaphragm;
said venting means comprising a venting line housed in said control unit and communicating with said control chamber, and a venting aperture at one end of said venting line, said closure element being arranged adjacent said venting aperture;
said electrically operated closure element comprising a magnitizable core and an exciter winding, said core extending parallel and in spaced relation to a wall of the control unit containing said venting aperture, two magnetizable straps extending transversely of the core and securing the ends of said core, a lever coupled with one of said straps for pivotal movement to a position opening said venting aperture when the coil is energized, and a restoring spring to bias the lever to a position closing said venting aperture.

6. A dental unit comprising:
dental handpieces operable by pressure medium;
a holder for each handpiece;

a control unit operable to control the supply of pressure medium to each handpiece;

and switch means associated with each holder and with said control unit, each switch means being operable upon removal of the respective handpiece from its holder to initiate operation of the control unit for the supply of pressure medium to the handpiece;

said control unit comprising:

a control block corresponding to each handpiece;

a first passage extending through said control blocks and communicable with a supply of pressure medium for operating the handpieces;

a second passage in each control block communicable with said first passage for supplying pressure medium to the handpiece corresponding to the control block;

a diaphragm associated with each of said second passages and operable to control the communication between the respective second passage and said first passage;

a control chamber provided on one side of each diaphragm;

a control line communicable with each control chamber for supplying a control pressure medium to the control chamber to operate the diaphragm for blocking of communication between said first passage and said second passage;

venting means communicating with each control line for discharging control pressure medium from the respective control chamber for operating the diaphragm to permit communication between said first passage and said second passage when the venting means is open;

an electrically operable closure device cooperable with each of said venting means, said closure device being controlled by one of said switch means for opening of the venting means when a respective handpiece is removed from its holder said control line having a diaphragm controlled separately by pressure medium, one closure device influencing pressure conditions in said control chamber across said diaphragm;

said venting means comprising a venting line housed in said control unit and communicating with said control chamber, and a venting aperture at one end of said venting line, said closure element being arranged adjacent said venting aperture; said electrically operated closure element comprising a magnetizable core displaceably mounted in a stationary coil for movement when the coil is energized in an opening direction away from said venting aperture, and a restoring spring for biasing the core to a closed position with respect to the venting aperture; each closure element including a packing for sealing engagement with said venting aperture; and electrically operable handpieces, said control unit including control block associated with said electrically operated handpieces, a plurality of coolant passages extending through all of the control block of the control unit for conveying coolant media to said handpieces, branch passages provided in said control block and communicable with said coolant passages, a diaphragm arranged in the flow passed between each branch passage and one of said coolant passages to control the communication therebetween, a control chamber controlling the operation of the diaphragm, and means connecting said control chamber with a control line of the remaining control chambers.

* * * * *